United States Patent [19]

Walker et al.

[11] 4,252,680

[45] Feb. 24, 1981

[54] OXIDATIVE DEHYDROGENATION CATALYST PREPARATION

[75] Inventors: Darrell W. Walker; Floyd Farha, Jr., both of Bartlesville, Okla.

[73] Assignee: Phillips Petroleum Company, Bartlesville, Okla.

[21] Appl. No.: 99,273

[22] Filed: Dec. 3, 1979

[51] Int. Cl.³ .................. B01J 27/14; B01J 27/02; C07C 5/09
[52] U.S. Cl. ................... 252/435; 252/437; 252/439; 585/623
[58] Field of Search ............. 252/435, 437; 585/623

[56] References Cited

U.S. PATENT DOCUMENTS

| 3,775,508 | 11/1973 | Pitzer | 260/680 E |
| 4,010,114 | 3/1977 | Walker et al. | 252/437 |

*Primary Examiner*—Delbert E. Gantz
*Assistant Examiner*—William G. Wright

[57] ABSTRACT

In the precipitation of a tin-containing component and a phosphorus-containing component from an acid solution with a base to prepare a catalyst of improved selectivity to produce diolefin from corresponding monoolefin there is used with the base, or thereafter, a water-soluble sulfide. The water-soluble sulfide can be at least one of an alkali-and an alkaline earth metal sulfide and ammonium sulfide.

7 Claims, No Drawings

OXIDATIVE DEHYDROGENATION CATALYST PREPARATION

BRIEF SUMMARY OF THE INVENTION

In the preparation of a catalyst for the production of a conjugated diolefin by the oxidative dehydrogenation of the corresponding mono-olefin wherein the catalyst is a composition containing oxides of tin, phosphorus, and an element from groups IA and/or IIA of the periodic table of the elements and wherein the combining of the tin-containing component with the phosphorus-containing component is effected by precipitating these components simultaneously from an acid solution with a base such as ammonium hydroxide, at least a portion of the ammonium hydroxide is replaced with a water-soluble inorganic sulfide, e.g., an alkali-and/or alkaline earth metal sulfide and ammonium sulfide.

DETAILED DESCRIPTION

In one of its aspects this invention relates to the oxidative dehydrogenation process in which a catalyst is employed to convert a mono-olefin to a conjugated diolefin. In one of its aspects the invention relates to the preparation of an improved catalyst for the oxidative dehydrogenation just described. In another of its aspects the invention relates to the catalyst as produced.

In one of its concepts the invention provides a method as described herein wherein at least a portion of the alkali hydroxide, e.g., the ammonium hydroxide, employed to precipitate simultaneously the tin-containing and the phosphorus-containing component is, at least in part, replaced with an alkali-and/or alkaline earth metal sulfide and ammonium sulfide for example, lithium sulfide, sodium sulfide, potassium sulfide, rubidium sulfide, cesium sulfide, magnesium sulfide, calcium sulfide, strontium sulfide, and barium sulfide. In a more specific concept of the invention, about ten to about sixty percent of the ammonium hydroxide is replaced with an equivalent quantity of the selected sulfide. In a still more specific concept of the invention, in its now completed form, from about 33 to about 50 percent of the, say, ammonium hydroxide is replaced by sulfide. e.g., ammonium sulfide.

It is an object of this invention to prepare a catalyst suited to the oxidative dehydrogenation of a mono-olefin to produce a conjugated diolefin. It is the further object of the invention to prepare a catalyst described in the art, as above set forth, which will be more selective, as distinguished from more active, to make diolefins from mono-olefins in an oxidative dehydrogenation reaction.

Other aspects, concepts, objects, and several advantages of the invention are apparent from a study of this disclosure and the appended claims.

According to the present invention, the precipitation of the tin-containing component together with the phosphorus-containing component from acid solution, is accomplished by replacing at least part of the ammonium hydroxide or base with a sulfide as herein described.

Also, according to the present invention, some or all of the sulfide replacement for the ammonium hydroxide can be added to perform an anion exchange type reaction following upon the precipitation of the prior art mass with use of ammonium hydroxide or base only.

Without wishing in any way to be limited thereto, the following is an explanation or a view which may be given of the operation of the present invention: The presence of the sulfide ion in the preparation of the final catalyst, as can be seen from the data presented herein, provides a catalyst which is more selective, as distinguished from the more active, to make diolefins from mono-olefins in the OXD reaction.

Essentially then, however reached, the final composition, according to the present invention, will contain sulfur in chemically combined form. There will be no free ammonium sulfide that is the salt present in the catalyst when it is calcined to remove the heat-decomposable and heat-volatile ammonium salt according to U.S. Pat. No. 3,775,508, column 4, lines 19–25.

The following examples illustrate the preparation of a catalyst according to this invention, and also some results when the catalyst is compared with a control in oxidative dehydrogenation of n-butene under reaction conditions.

EXAMPLE 1

The preparation of a control, Catalyst A, and a catalyst according to this invention, Catalyst B, is described here.

Catalyst A

A tin- and phosphorus-containing solution was prepared by combining 33.8 gm of 85% $H_3PO_4$ (0.293 moles) in 150 cc of water with 153.8 gm of $SnCl_4.5H_2O$ (0.439 moles) dissolved in 300 cc of water. This solution and a solution containing 140 cc of concentrated ammonium hydroxide (2.12 moles) in 800 cc of water were simultaneously added dropwise to 200 cc of water at a rate that maintained the pH of the mixture between 3 and 4. The final pH was 3.5. This slurry was allowed to stand at ambient conditions for about 48 hours and was then filtered. The gel was washed four times with one liter portions of water; it remained in the fourth wash nearly three days before being filtered. The gel was dried at 110° C. in a forced draft oven, yielding 87 gm of white solid that contained 0.05 weight percent chloride by calculation. This material was ground to pass a 40 mesh sieve, then impregnated with 18.0 gm (0.261 moles) of lithium nitrate dissolved in 120 cc of water and dried at 120° C. overnight. The lithium-treated material was again passed through a 40 mesh sieve, mixed with three gm of polyethylene powder to serve as a lubricant and tabletted into ¼" diameter by about 1/10" tablets.

Catalyst B

A tin- and phosphorus-containing solution was prepared by combining 33.8 gm of 85% $H_3PO_4$ (0.293 moles) in 150 cc of water with 153.8 gm of $SnCl_4.5H_2O$ (0.439 moles) dissolved in 300 cc of water. This solution and a solution containing 70 cc of concentrated ammonium hydroxide (1.06 moles) and 162 gm of 21% $(NH_4)_2S$ (0.50 moles) in 800 cc of water were simultaneously added dropwise to 200 cc of water at a rate that maintained the pH of the mixture between 3 and 4. About 25 gm of additional ammonium sulfide reagent solution was finally added, yielding a slurry having pH 3.5. After standing for nearly three days at ambient conditions the gel was filtered and washed four times with one liter portions of water, being allowed to stand in the final wash overnight before filtering. The gel was dried at 120° C. in a forced draft oven, to yield 102 gm of brown solid that contained 0.07 weight percent chloride by calculation. It was crushed to pass a 40 mesh sieve, then impregnated with 18.0 gm (0.261 moles) of lithium nitrate dissolved in 60 cc of water. After drying at 120° C. it was again passed through a 40 sieve, mixed with three gm of powdered polyethylene that served as a lubricant and tabletted in ¼" diameter by about 1/10" tablets.

Both tabletted materials (Catalysts A and B) were heat treated concurrently in air, in a muffle furnace, on the following schedule: two hours from ambient to 482° C., hold 4 hours at 482° C., 4 hours from 482° C. to 649° C., and finally hold at 649° C. for 4 hours before cooling to room temperature. After this treatment both catalysts were weak and powdery. They were pressed in a laboratory hydraulic press under conditions where some powders become hard and rugged, but Catalyst B remained weak and crumbly; Catalyst A was somewhat firmer. Both catalysts were screened, and the −8+16 mesh U.S. sieve fractions were retained for testing.

EXAMPLE 2

Catalysts A and B, together with some nominally identical specimens that were prepared as these were, but at different times, were tested to measure their activity for oxidative dehydrogenation of butene-2 to butadiene. All tests reported here were made on catalysts that had been calcined at 649° C. Separate tests had shown that catalyst A calcined at 538° C. prior to testing at that temperature or at 566° C. was significantly more selective than those calcined at the higher temperature, whereas Catalyst B was virtually unaffected by calcining temperature. These tests were made using butene at 600 gas hourly space velocity, a 4:1 air:butene-2 volume ratio, and an 18:1 steam:butene-2 volume ratio, at atmospheric pressure. Table I summarizes results of these tests.

TABLE I

| Test No. | Catalyst* | Reaction temp., °C. | Butene conv., % | Gas phase selectivity to butadiene, %** |
|---|---|---|---|---|
| 1 | A | 538 | 60 | 89.9 |
| 2 | A' | 538 | 80 | 95.6 |
| 3 | A' | 566 | 87 | 91.5 |
| 4 | A'' | 566 | 80 | 89.1 |
| 5 | B | 538 | 52 | 98.7 |
| 6 | B' | 538 | 51 | 96.0 |
| 7 | B'' | 538 | 42 | 98.2 |
| 8 | B' | 566 | 63 | 97.6 |
| 9 | B'' | 566 | 66 | 96.7 |
| 10 | B''' | 566 | 80 | 96.2 |

*All A's prepared by precipitation with ammonium hydroxide only; all B's prepared by precipitation with half ammonium hydroxide and half ammonium sulfide.
**This ignores products that were dissolved in the condensed steam and were absent from gas phase analyses.

Table II reports the average test results from Table I for Catalysts A and B at the two temperatures that were used.

TABLE II

| Test No. | Catalyst | Reaction temp., °C. | Butene conv., % | Gas phase selectivity to butadiene, % |
|---|---|---|---|---|
| 1-2 | All A | 538 | 70.0 | 92.8 |
| 3-4 | All A | 566 | 83.5 | 90.3 |
| 5-7 | All B | 538 | 48.3 | 97.6 |
| 8-10 | All B | 566 | 69.7 | 96.8 |

Table II shows that Catalyst B gives higher selectivity and lower conversion than Catalyst A when operated at the same temperature. However, when temperature is adjusted to obtain the same conversion level with the two catalysts, Catalyst B gives four percentage points higher selectivity than Catalyst A, a distinct advantage.

Reasonable variation and modification are possible within the scope of the foregoing disclosure and the appended claims to the invention the essence of which is that in the preparation of an oxidative dehydrogenation catalyst suited for conversion of mono-olefin to diolefin, the catalyst having improved selectivity, the preparation of the catalyst comprising precipitating together a tin-containing component with a phosphorus-containing component from an acid solution with a base such as ammonium hydroxide, a sulfide is introduced into the precipitated mass, e.g., a water-soluble sulfide at least in part is substituted for the base and precipitation is caused to occur in the presence of said sulfide or, after precipitation with the base, there is added then to effect an anion exchange type reaction a water-soluble sulfide.

We claim:

1. A process for the preparation of an oxidative dehydrogenation catalyst suited for conversion of mono-olefin to the diolefin without excessive conversion of hydrocarbon by complete oxidation, the catalyst having improved selectivity, which comprises precipitating together a tin-containing component with a phosphorus-containing component from an acid solution with a base such as ammonium hydroxide and introducing sulfide into the precipitated mass.

2. A process according to claim 1 wherein at least a portion of the base to be used to cause the precipitation is replaced with a water-soluble sulfide so that precipitation occurs in the presence of said sulfide.

3. A process according to claim 1 wherein after precipitation with the base there is then added to effect an anion exchange type reaction the water-soluble sulfide.

4. A process according to claim 1 wherein the sulfide is at least one of an alkali-and an alkaline earth metal sulfide and ammonium sulfide.

5. A process according to claim 1 wherein the sulfide is at least one selected from lithium sulfide, sodium sulfide, potassium sulfide, rubidium sulfide, cesium sulfide, magnesium sulfide, calcium sulfide, strontium sulfide, and barium sulfide, and ammonium sulfide.

6. A process according to claim 1 wherein from about 10 to about 60 percent of the base is replaced with an equivalent quantity of sulfide.

7. A process according to claim 1 wherein from about 33 to about 50 percent of the base is replaced by the sulfide.

* * * * *